US005209978A

United States Patent [19]

Kosaka et al.

[11] Patent Number: 5,209,978

[45] Date of Patent: May 11, 1993

[54] SEAMLESS SOFT CAPSULE AND PRODUCTION THEREOF

[75] Inventors: Tadashi Kosaka, Ageo; Kazuki Omata, Tokyo; Tatsuo Hashimoto, Ageo; Teruaki Yamazaki, Ageo; Kazuo Hayashi, Ageo; Tomiya Hosoi, Saitama; Kenichi Ikuta, Okegawa, all of Japan

[73] Assignee: Taisho Pharmaceutical Co., Ltd., Japan

[21] Appl. No.: 774,325

[22] Filed: Oct. 10, 1991

Related U.S. Application Data

[60] Division of Ser. No. 296,377, Dec. 28, 1987, abandoned, which is a continuation of Ser. No. 942,690, Dec. 17, 1986, abandoned.

[30] Foreign Application Priority Data

Dec. 26, 1985 [JP] Japan .................................... 297182

[51] Int. Cl.[5] ...................... A61K 9/64; B01J 13/06; B29C 39/10

[52] U.S. Cl. .................................. 428/402.2; 264/4; 264/4.3; 264/4.4; 424/455; 424/456; 424/492; 424/493; 425/5; 514/962; 514/963

[58] Field of Search ........................... 264/4.4, 4, 4.3; 428/402.2; 424/455, 456, 492, 493; 514/962, 963

[56] References Cited

U.S. PATENT DOCUMENTS

| | | | |
|---|---|---|---|
| 2,339,114 | 1/1944 | Scherer | 264/4 |
| 3,041,289 | 6/1962 | Katchen et al. | 264/4.4 X |
| 3,576,660 | 4/1971 | Bayless et al. | 264/4.4 X |
| 3,636,922 | 1/1972 | Ketner | 604/289 X |
| 4,627,850 | 12/1986 | Deters et al. | 424/457 X |

FOREIGN PATENT DOCUMENTS

| | | | |
|---|---|---|---|
| 0116311 | 8/1984 | European Pat. Off. . | |
| 0040056 | 3/1985 | Japan | 264/4 |

OTHER PUBLICATIONS

Patent Abstracts of Japan, 8 and 10, Nr. 350 (C-387) [2406], Nov. 26, 1985.

Patent Abstracts of Japan, vol. 9, No. 254 (C-308) [1977], Oct. 11, 1985.

*Primary Examiner*—Richard D. Lovering

*Attorney, Agent, or Firm*—Lorusso & Loud

[57] ABSTRACT

A soft capsule composed of a plurality of cells coalesced to each other and filling substances encapsulated in the individual cells, the wall of at least one of the cells being formed of a material different from a material forming the wall of at least one of the other cells, and said capsule being seamless. The soft capsule can be produced by (a) preparing a plurality of composite jet streams each consisting of a stream of a film-forming liquid substance for forming a cell wall and within said stream of a film-forming liquid substance a single stream, or a plurality of independent streams, of a filling substance having flowability, the film-forming liquid substance in at least one of the composite jet streams being different from the film-forming liquid substance in at least one of the other composite jet streams, (b) advancing the plurality of composite jet streams in closely spaced relationship into and through a stream of a liquid medium substantially incapable of dissolving the film-forming liquid substance in the flowing direction of the liquid medium stream, (c) coalescing the adjacent composite jet streams to each other to form a single composite jet stream in the liquid medium stream, (d) cutting the single composite jet stream to a predetermined length successively from its leading end in the liquid medium stream, and (e) solidifying the cell walls of the resulting soft capsule.

8 Claims, 2 Drawing Sheets

SEAMLESS SOFT CAPSULE AND PRODUCTION THEREOF

This application is a division of application Ser. No. 07/296,377, filed Dec. 28, 1987, now abandoned, which is a continuation of application Ser. No. 06/942,690, filed Dec. 17, 1986, now abandoned.

This invention relates to a seamless soft capsule, and more specifically, to a seamless soft capsule having a multicellular structure, and a method of its production.

A multicellular soft capsule having its inside partitioned by a film was recently proposed (see Japanese Laid-Open Patent Publication No. 109520/1985). This patent document states that the multicellular soft capsule is obtained by partitioning a soft capsule shell composed of an upper film and a lower film into two cells by means of a partitioning film, and filling different drugs into the two cells. As a result, two drugs which are not desired to be mixed can be stably included in a single soft capsule. By using materials having different solubilities and dissolving speeds, it is possible to cause one part of a single capsule to be released and absorbed in the stomach and the other part, in the intestines. It is also possible to make one part of the capsule fast-releasing and the other part slow-releasing.

Since the proposed multicellular soft capsule is produced by a rotary method or a flat plate method, the capsule shell has seams. Hence, in spite of the aforesaid advantages, it has the defect that the filled drugs leak from the seams, or air comes through the seams to deteriorate the contents oxidatively. Furthermore, by the rotary method or the flat plate method, it is difficult to produce multicellular soft capsules having a small size, and moreover, the cost of production becomes high. Furthermore, since both surfaces of the partitioning film in the aforesaid multicellular soft capsule are formed of the same material, if a drug to be filled in one of the cells reacts with the components of the partitioning film, it cannot be included in such a capsule.

It is an object of this invention to provide a multicellular seamless soft capsule free from the aforesaid defects.

Another object of this invention is to provide a simple and inexpensive method of producing the aforesaid seamless soft capsule, which can easily give capsules of a small size as well.

Further objects and advantages of this invention will become apparent from the following detailed description.

According to one aspect of this invention, there is provided a soft capsule composed of a plurality of cells coalesced to each other and filling substances encapsulated in the individual cells, the wall of at least one of the cells being formed of a material different from a material forming the wall of at least one of the other cells, and said capsule being seamless.

According to another aspect of this invention, the seamless soft capsule of this invention is produced by a method which comprises (a) preparing a plurality of parallel, side-by-side composite jet streams each having a central longitudinal axis and consisting of a stream of a film-forming liquid substance for forming a cell wall and within said stream of a film-forming liquid substance a single stream, or a plurality of independent streams, of a filling substance having flowability, the film-forming liquid substance in at least one of the composite jet streams being different from the film-forming liquid substance in at least one of the other composite jet streams, (b) advancing the plurality of composite jet streams with their respective central longitudinal axes in a spaced and parallel relationship into and through a stream of a liquid medium substantially incapable of dissolving the film-forming liquid substance in the flowing direction of the liquid medium stream, (c) coalescing the adjacent composite jet streams to each other to form a single composite jet stream in the liquid medium stream, (d) cutting the single composite jet stream to a predetermined length successively from its leading end in the liquid medium stream, and (e) solidifying the cell walls of the resulting soft capsule.

BRIEF DESCRIPTION OF THE DRAWINGS

The capsule and the method of producing it in accordance with this invention will be specifically described with reference to the accompanying drawings in which:

In FIG. 1, the reference numeral 1 represents a tank holding a film-forming liquid substance A for forming a cell wall; 2, a tank holding a film-forming substance B which is different from the substance A; 3, a tank holding a filling substance C; and 4, a tank holding another filling substance D. The tanks 1, 2, 3 and 4 are individually provided with heating means (not shown) for maintaining the substances A, B, C and D at suitable temperatures for maintaining them flowable. The substances A, B, C and D are supplied to the tanks 1, 2, 3 and 4 respectively. Metering pumps 11, 21, 31 and 41 are provided for feeding the substances A, B, C and D of the tanks 1, 2, 3 and 4 to a composite nozzle 5. The composite nozzle 5, as shown in FIGS. 1 and 2, is a duplex nozzle consisting of outside nozzles 51 and 52 having a semielliptical cross sectional shape resulting from partitioning an elliptical tube by a partitioning wall 50 at its center and inside nozzles 5*a* and 5*b* of a smaller diameter disposed nearly centrally in the outside nozzles 51 and 52 respectively. The outside nozzles 51 and 52 communicate with the tanks 1 and 2, and the inside nozzles 5a and 5b, with the tanks 3 and 4. The composite nozzle 5 faces downwardly along a downwardly flowing stream of a liquid medium e within a capsule-forming tank 6.

Figure 2:
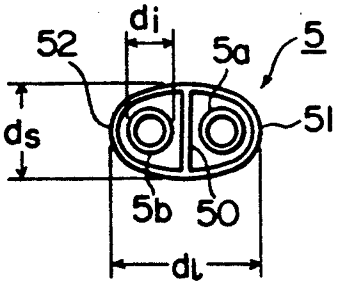
FIG. 2 is an enlarged end view of a composite nozzle in the apparatus shown in FIG. 1.

The specification of the composite nozzle 5 may be freely changed according, for example, to the use of the capsule to be produced. For example, for use in making a capsule used as a medicine, a typical specification is that in FIG. 2, the elliptical tube has an outside long diameter $d_l$ of 5 to 20 mm and an outside short diameter $d_s$ of 3 to 12 mm, and the inside nozzles have an outside diameter of $d_i$ of 2 to 9 mm, and the individual tubes have a thickness of 0.1 to 2 mm.

The liquid medium e formed, for example, of liquid paraffin is sent to a heat exchanger 72 from a recovery hopper 7 concurrently acting as a storage tank by means of a pump 71. In the heat exchanger 72, it is cooled to a moderate temperature of, for example, about 5° C. and supplied to the upper portion of the capsule-forming tank 6. It becomes a downwardly flowing stream within the capsule-forming tank 6, and is circulated to the recovery hopper 7 via a capsule recovery tube 61. A part of the liquid medium e is supplied to a pulse stream-forming device 74 by means of a pump 73 from the hopper 7. It is converted to a regular pulse stream in the pulse stream-forming device 74 and supplied to a pulse stream nozzle 8 provided within the capsule-forming tank 6.

The pulse stream nozzle 8 is a circular nozzle provided immediately below, and coaxially with, the composite nozzle 5 and having a slightly larger diameter than the diameter of the elliptical tube of the composite nozzle 5. A pulsating stream of the liquid medium e from the nozzle 8 is extruded toward the center of the nozzle 8 from an annular slit formed within the nozzle 8 in such a manner as to surround a single composite jet stream formed by the composite nozzle 5

Film-forming liquid substances A and B for cell wall formation and filling substances C and D to be filled in a capsule are sent under pressure to nozzles 51, 52, 5a and 5b constituting the composite nozzle 5 by means of the metering pumps 11, 21, 31 and 41. From the nozzle 51, a composite jet stream composed of a stream of the film-forming substance A and a single stream of the filling substance C is extruded into, and along, the downwardly flowing liquid medium flow within the capsule-forming tank 6, and from the nozzle 52, a composite jet stream composed of a stream of the film-forming substance B and a stream of the filling substance D is likewise extruded into, and along, the downwardly flowing liquid medium stream within the capsule-forming tank 6. Since the nozzles 51 and 52 form an integral unit via a partitioning wall 50, the two composite jet streams extruded as above, nearly simultaneously with their formation, are coalesced to each other into a single composite jet stream within the downwardly flowing stream of the liquid medium e owing to the surface tensions of the film-forming liquid substances A and B.

The speeds of extruding the composite jet streams, and the flow rate of the downwardly flowing stream of the liquid medium e can be varied depending upon, for example, the types of the film-forming liquid substances forming the composite jet streams, the type of the liquid medium e, and the size of the composite nozzle, and any skilled person in the art would be able to determine optimum conditions easily by routine experiments. As tentative standards, it is convenient to adjust the extruding speed of each composite jet stream to about 4 to 40 m/min., and the flow rate of the downwardly flowing liquid medium stream to about 5 to 50 m/min.

Figure 1:
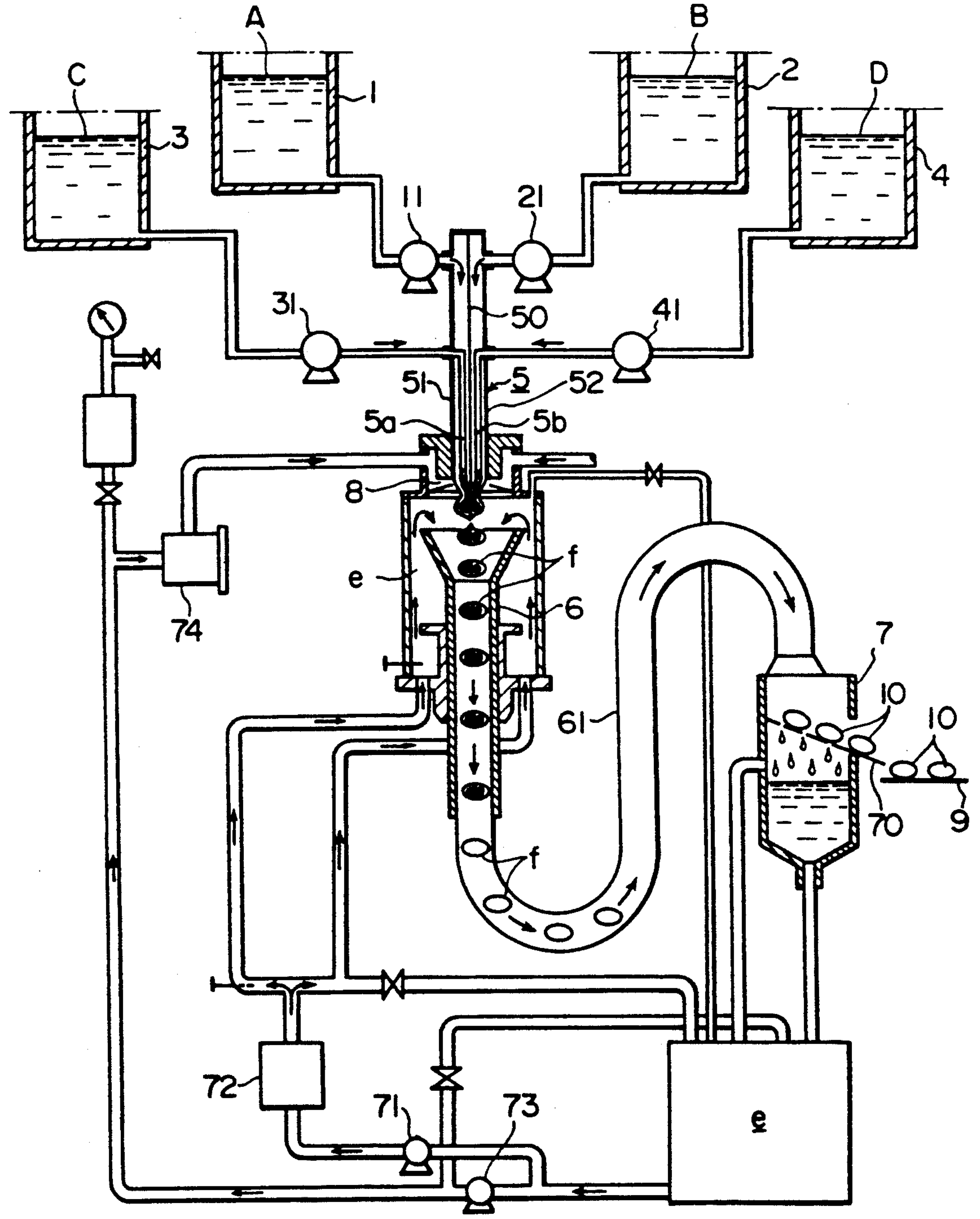
FIG. 1 is a systematic view, partly in section, of one example of an apparatus used to practice the method of this invention in its entirety.

The single composite jet stream so formed undergoes impact of the regular pulse stream of the liquid medium e from the pulse stream nozzle 8, whereby as shown in FIG. 1, necks or narrowed parts are formed at certain intervals beginning with its leading end. The jet stream is drawn downwardly by the downwardly flowing stream of the liquid medium e, and successively cut off at the neck portions by the downwardly drawing force. Each cut droplet f contains the filling substances C and D encapsulated in the film-forming liquid substances A and B by the surface tension of the substances A and B, and is formed into a seamless capsule, which is roundish as a whole, while moving down through the downwardly flowing stream of the liquid medium e. The capsules formed advance to the hopper 7 via the recovery tube 61 while being cooled and solidified. In the hopper 7, the capsules are separated from the liquid medium e by a separator 70, supplied to a conveyor 9 provided on one side of the separator 70, and sent to a drying step where they are dried to produce a final product.

Figure 3:
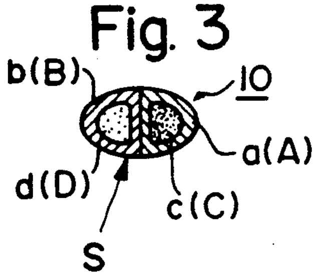
FIG. 3 is an enlarged sectional view of a seamless soft capsule produced in accordance with this invention by the apparatus of FIG. 1.

By the method described above, there are obtained unitary seamless soft capsules 10 in which a cell a formed of the film-forming substance A and the filling substance C encapsulated in it is coalesced to a cell b formed of the film-forming substance B which is different from the substance A and the filling substance D encapsulated in it, and the cell wall is of a double structure at the coalesced part, as shown in FIG. 3. Cell walls A and B are melded together with each of A and B forming a portion of the outermost surfaces of the capsule.

The film-forming substance for cell formation may be any material which can be formed into a thin film from its melt or solution, and after film formation can be solidified by cooling and/or drying. Substances usually employed in forming the shell of a soft capsule may be used in this invention. Examples include film-forming substances composed of gelatin or gelatin derivatives such as succinic gelatin and incorporated therein, plasticizers [such as glycerol, sorbitol, propylene glycol and Carbowax (polyethylene glycol)], essences and flavors (such as peppermint oil, cinnamon oil and strawberry), dyes (such as yellow No. 4, yellow No. 5, red No. 1, blue No. 1 and copper chlorophyllin), opacifying agents (such as titanium dioxide and red iron oxide), solubility controlling agents (such as cellulose acetate phthalate, alkali metal salts of hydroxypropylmethyl cellulose, alkali metal salts of hydroxymethyl cellulose acetate succinate, alkali metal salts of alginic acid, alkali metal salts of polyacrylic acid, methyl cellulose, carboxymethyl cellulose, casein, collagen, agar powder, polyvinyl alcohol and pectin)), etc. selected as desired. It is generally used as a liquid by dissolving it in water under heat.

The filling substance to be encapsulated in each cell of the soft capsule of this invention can be any drug which does not dissolve the cell wall nor react with the components of the cell wall. It is preferably liquid when it is to be filled in the cell in accordance with the method of this invention. Accordingly, when the drug is a solid, it is desirably filled in a flowable state as a solution, emulsion or suspension.

According to the method of this invention, by using a combination of two or more suitable film-forming substances selected from those exemplified above, at least one of a plurality of cells constituting the resulting soft capsule can have a different dissolving time in the digestive tract from at least one of the other cells (for example, whether fast-releasing or slow-releasing), or at least one cell may have different dissolving characteristic from at least one of the other cells (for example, whether released and adsorbed in the stomach or the intestines).

Furthermore, in the present invention, the filling substances to be encapsulated in the cells may be varied from cell to cell. As a result, a single capsule may be obtained in which a drug expected to be fast-acting is filled in a fast-dissolving cell and a drug desired to be slow-acting is filled in a slow-dissolving cell. Alternatively, a single capsule cell may be obtained in which a drug expected to develop its effect in the stomach is filled in a cell soluble at the stomach, and another drug expected to develop its effect in the intestines is filled in a cell soluble at the intestines.

The shape of the soft capsule 10 can be selected by changing the shape of the end surface of the composite nozzle 5 on the extrusion side. Some modified examples of the composite nozzle 5 will be described below.

Figure 4:
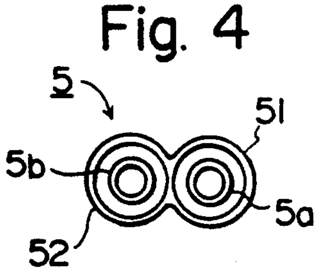
FIG. 4 is an end view showing another example of the composite nozzle.
Figure 5:
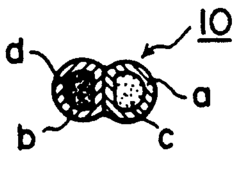
FIG. 5 is a sectional view of a seamless soft capsule produced by using the composite nozzle of FIG. 4.

The composite nozzle 5 shown in FIG. 4 is composed of duplex outside nozzles 51 and 52 having a cocoon-shaped cross section and smaller-diameter inside nozzles 5*a* and 5*b* disposed coaxially within the outside nozzles 51 and 52 respectively. The capsule 10 obtained by using this composite nozzle 5 has a cocoon-shaped cross-section as shown in FIG. 5. It is a seamless soft capsule in which filling substances c and d are independently encapsulated in cells a and b.

Figure 6:
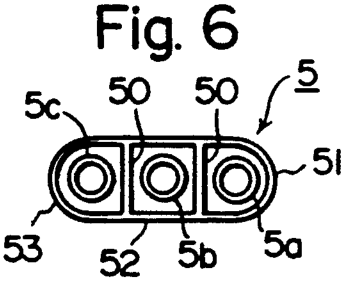
FIG. 6 is an end view of still another example of the composite nozzle.
Figure 8:
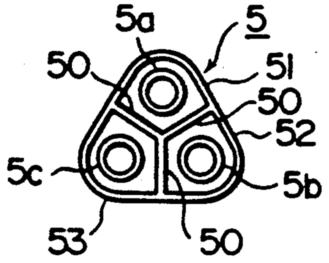
FIG. 8 is an end view of yet another example of the composite nozzle.
Figure 7:
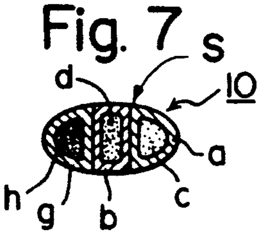
FIG. 7 is a sectional view of a seamless soft capsule produced by using the composite nozzle of FIG. 6.
Figure 9:
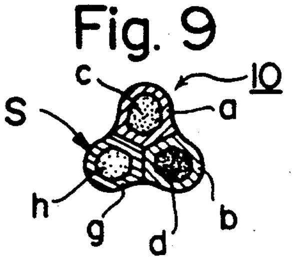
FIG. 9 is a sectional view of a seamless soft capsule produced by using the composite nozzle of FIG. 8.

FIGS. 6 and 8 show other examples of the composite nozzle 5. These nozzles 5 are each divided into three outside nozzles 51, 52 and 53 by two or three partitioning walls 50 and smaller-diameter inside nozzles 5*a*, 5*b* and 5*c* are disposed centrally in the outside nozzles 51, 52 and 53 respectively. By simultaneously extruding different film-forming substances from the outside nozzles 51, 52 and 53 and filling substances from the inside nozzles 5*a*, 5*b* and 5*c* with the use of these composite nozzles 5, there can be produced seamless soft capsules 10 in which the filling substances c, d and h are encapsulated in the cells a, b and g formed from cell walls of different materials, as shown in FIGS. 7 and 9.

Figure 10:
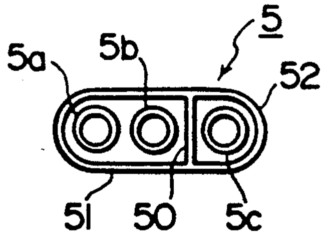
FIG. 10 is an end view of a further example of the composite nozzle.

FIG. 10 shows still another example of the composite nozzle 5 in which a large-diameter tube of an elliptical cross-sectional shape is divided into a large-diameter outside nozzle 51 and a small-diameter outside nozzle 52 by a partitioning wall 50 at a site about ⅓ as viewed from one end surface of the tube, inside nozzles 5*a* and 5*b* having a smaller diameter are disposed in the large-diameter outside nozzle 51 in spaced-apart relationship, and an inside nozzle 5*c* having a smaller diameter is disposed centrally in the small-diameter outside nozzle 52.

When the composite nozzle 5 shown in FIG. 10 is used, different film-forming substances and different filling substances are simultaneously extruded along the stream of the liquid medium in the apparatus shown in FIG. 1 from the outside nozzles 51 and 52, and the inside nozzles 5*a*, 5*b* and 5*c*, respectively. Thus, a composite jet stream containing two independent streams of the filling substances c and h and a composite jet stream containing one stream of the filling substance b are formed simultaneously in the capsule-forming tank 6 as in FIG. 1, and coalesced into a single composite jet stream. The single composite jet stream is successively cut in a predetermined size from its leading end in the flowing direction by the action of the pulsating flow of the liquid medium.

Figure 11:
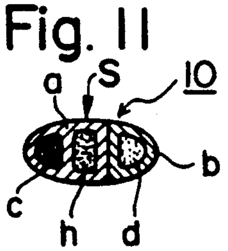
FIG. 11 is a sectional view of a soft capsule produced by using the composite nozzle of FIG. 10.

The soft capsule 10 produced in this way is a seamless soft capsule composed of a unitary structure of a cell a and two filling substances c and h independently encapsulated in it and a cell b and one filling substance d encapsulated in it, as shown in FIG. 11.

The soft capsule 10 shown in FIG. 11 and the method of production using the composite nozzle shown in FIG. 10 give a capsule in which two filling substances c and h are independently encapsulated in a cell having a cell wall of the same material. Hence, they are beneficial when different drugs which are to be released simultaneously from one cell a but should not be mixed beforehand are used as the filling substances c and h.

Figure 12:
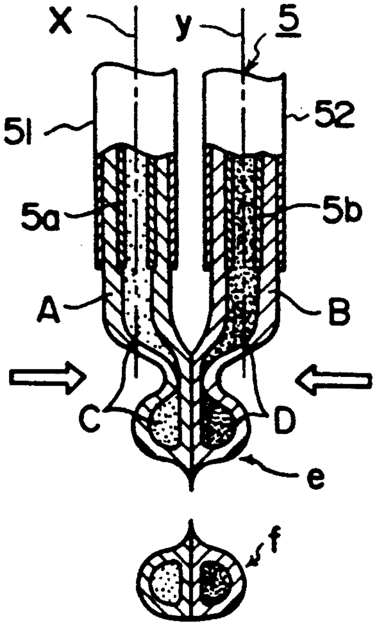
FIG. 12 is an enlarged sectional view of the principal parts of a still further example of the composite nozzle.

Even when the outside nozzles 51 and 52 of the composite nozzle 5 are not unitary but are slightly spaced from each other as shown in the embodiment given in FIG. 12, composite jet streams having spaced and parallel central longitudinal axes "x" and "y" are extruded separately from the nozzles 51 and 52 are coalesced into a single composite jet stream by the pulsating flow of the liquid medium, and cut to a predetermined length from its leading end in the flowing direction. Hence, the method of this invention can be practiced in the same way by using the composite nozzle 5 shown in FIG. 12.

The single composite jet stream formed along the flow of the liquid medium e may be cut to a predetermined length from its leading end in the flowing direction by intermittently increasing the speed of the downwardly flowing stream of the liquid medium e, and intermittently pulling off the composite jet stream downwardly by the quickened downwardly flowing liquid stream, instead of applying a pulsating flow of the liquid medium e sideways to the composite jet stream in the embodiments described above. By this alternative procedure, too, the single composite jet stream can be cut successively to a predetermined length.

According to this invention, one capsule contains a plurality of cells whose cell walls are made of different materials. Hence, the present invention is suitable for filling both a substance to be released and absorbed in the stomach and a substance to be released and absorbed in the intestines, or at least two substances having different dissolving times, in a separated state in a single capsule. Since the soft capsule of the invention is seamless, the filled substances can be retained stably while preventing their deterioration by oxidation or otherwise. According to the method of this invention, capsules of any desired sizes can be produced, and capsules having a smaller size than in the prior art can be easily produced at low cost.

The following Example illustrates the present invention more specifically.

EXAMPLE 1

Referring to FIG. 1, a film-forming substance A was filled in tank 1, and a film-forming substance B, in tank 2. These film-forming substances A and B were extruded from composite nozzle 5 having a outside long diameter ($d_l$) of 13 mm, an outside short diameter ($d_s$) of 9 mm and a thickness of 1 mm (FIG. 2) by metering pumps 11 and 21. The amount of each of the film-forming substances A and B was 65.7 g/min.

In the meantime, a filling substance C was filled in tank 3, and another filling substance D, in tank 4. The filling substances C and D were extruded from nozzles 5*a* and 5*b* having an outside diameter (di) of 3 mm, an inside diameter of 2 mm and a thickness of 0.5 mm (FIG. 2) by metering pumps 31 and 41. The amount of each of the filling substances extruded was 36 g/min. Composite jet streams composed of the film-forming substances A and B and the filling substances C and D flowed at a rate of 10 meters/min.

A paraffin oil as a cooling medium e within vessel 7 and heat-exchanger 72 was maintained at 3° C., and flowed downwardly in capsule-forming tank 6 at a flow rate of 15 m/min. A pulsating flow of the paraffin oil generated from pulse flow generator 74 was extruded at equal time intervals from pulse flow nozzle 8 accurately 15 times per second.

Within the capsule-forming tank, capsules were formed at a rate of 15 per second at intervals of about 11 mm. After drying, each of the capsules had a long diameter of 8 mm and a short diameter of 6 mm, and the amount of each of the filling substances was 40 mg per capsule.

The film-forming substance A is a solution consisting of 20 parts of gelatin, 5 parts by weight of glycerol, 8 parts by weight of sorbitol and 67 parts by weight of purified water which was maintained at about 60° C.

The film-forming substance B was a solution consisting of 18 parts by weight of gelatin, 5 parts by weight of glycerol, 2.5 parts by weight of sodium alginate and 74.5 parts by weight of purified water which was maintained at about 60° C.

The filling substances C and D were solutions composed of different drugs which were maintained at about 25° C.

By the above procedure, there was produced a seamless soft capsule 10 which contained a core c composed of the filling substance C encapsulated in a gastric-soluble film a composed of the film-forming substance A and a core d composed of the filling substance D encapsulated in an enteric-soluble film b independently from each other, with the film portion separating the core c from the core d being of a double structure.

When the resulting soft capsule 10 was immersed in the first solution (gastric juice) stipulated in the Revised Method of Testing Disintegration in accordance with Japanese Pharmacopoeia, the film a dissolved in several minutes to release the core c, whereas the film b did not dissolve for more than 2 hours.

When the soft capsule 10 was immersed in the second solution (intestinal fluid) in the Revised Method of Testing Disintegration in accordance with Japanese Pharmacopoeia, both the films a and b dissolved within 2 to 3 minutes.

EXAMPLE 2

In the same way as in Example 1, film-forming substances A and B were extruded from a composite nozzle having an outside long diameter ($D_l$) of 7.5 mm, an outside short diameter ($D_s$) of 3.5 mm and a thickness of 0.5 mm. The amount of each of the film-forming substances A and B extruded was 21.9 g/min.

In the meantime, filling substances C and D were extruded from nozzles 5*a* and 5*b* having an outside diameter ($d_i$) of 1 mm and a thickness of 0.1 mm. The amount of each of the substances C and D extruded was 18.6 g/min. The speed of the composite jet stream at this time was 6 m/min. A paraffin oil was used as a cooling medium e and caused to flow in capsule-forming tank 6 at a rate of 22.5 m/min.

A pulsating flow of the paraffin oil generated from the pulse stream generator 74 was extruded from pulse stream nozzle 8 at equal time intervals accurately 50 times per second.

In capsule-forming tank 6, fifty capsules were formed per second at intervals of about 7.5 mm. After drying, each of the capsule had a long diameter of 3.5 mm and a short diameter of 2.5 mm. The amount of each of the filling substances C and D was about 6.2 mg.

What is claimed is:

1. A process for producing a soft capsule composed of a plurality of cells coalesced to each other and filling substances encapsulated in the individual cells, the wall of at least one of the cells being formed of a material different from a material forming the wall of at least a second of the cells, and said capsule being seamless, said method comprising:

(a) preparing a plurality of parallel, side by side composite jet streams, each of said composite jet streams having a central longitudinal axis and forming one of said plurality of cells, each of said composite jet streams consisting of a stream of a film-forming liquid substance for forming a cell wall and, within and surrounded by said stream of a film-forming liquid substance, a single stream, or a plurality of independent streams, of a filling substance, the film-forming liquid substance in at least one of the composite jet streams being different from the film-forming liquid substance in at least one of the other composite jet streams, (b) advancing the plurality of composite jet streams, with their respective central longitudinal axes in a spaced and parallel relationship, into and through a liquid medium substantially incapable of dissolving the film-forming liquid substance, (c) coalescing the film-forming streams of adjacent composite jet streams to each other to form a unitary composite jet stream in the liquid medium, (d) cutting the unitary composite jet stream to a predetermined length successively from its leading end in the liquid medium and, (e) solidifying the cell walls of the resulting cut pieces to form the soft capsule.

2. A soft capsule produced by the process of claim 1 wherein the wall of said one cell is adhered to the wall of said second cell to define an interface traversing the entire width of the capsule.

3. A soft capsule in accordance with claim 2 produced by said process using two of said composite jet streams and wherein said interface bisects said capsule.

4. A soft capsule produced by the process of claim 1 which is oblong in shape and has, in cross-section, one dimension equal to the corresponding dimension of one of said cells.

5. A soft capsule, triangular in cross-section, produced by the process of claim 1 utilizing three of said composite jet streams, said capsule consisting of three cells, each of said three cells being joined to the two other cells along an interface running from one triangular surface to a second triangular surface of said cross-section.

6. A unitary seamless capsule containing plural cells coalesced together, each of said cells containing a filling substance encapsulated by a cell wall completely surrounding the filling substance, the cell wall of at least one of the cells being formed of a material different from a material forming the wall of at least a second of said cells, said cell walls being melded together with each of said cell walls defining in part the outermost surface of said seamless capsule, said capsule having one cross-section cutting through all of said plural cells.

7. The unitary capsule of claim 6 wherein all of said plural cells are arranged in a linear array to define said cross-section.

8. The unitary capsule of claim 6 wherein all of said plural cells are arranged in a triangular array to define said cross-section.

* * * * *